United States Patent

Kramer et al.

[11] Patent Number: 5,326,236
[45] Date of Patent: Jul. 5, 1994

[54] COMPLIANT ROTOR FOR AN IMPROVED CARTRIDGE FOR DRUG INFUSION PUMP

[75] Inventors: Thomas A. Kramer, San Carlos; Mike Lawless, Poway; Stephen J. Kreinick, San Diego; John D. Gjata, La Jolla, all of Calif.

[73] Assignee: Abbott Laboratories, Abbott Park, Ill.

[21] Appl. No.: 126,461

[22] Filed: Sep. 24, 1993

[51] Int. Cl.⁵ .............................................. F04B 43/12
[52] U.S. Cl. ..................................... 417/476; 418/45; 417/474
[58] Field of Search ................. 417/474–478; 604/153, 154; 418/45, 57, 63

[56] References Cited

U.S. PATENT DOCUMENTS

| | | | |
|---|---|---|---|
| 1,543,163 | 6/1925 | Johnson et al. | 418/57 |
| 4,431,327 | 7/1984 | Mazzagatti | 418/57 |
| 4,472,116 | 9/1984 | Wenstrup | 604/153 |
| 4,559,040 | 12/1989 | Horres et al. | 417/476 |
| 5,057,081 | 10/1991 | Sunderland | 417/474 |

*Primary Examiner*—Richard A. Bertsch
*Assistant Examiner*—Peter Korytnyk
*Attorney, Agent, or Firm*—Harry G. Thibault; Robert E. Wexler

[57] ABSTRACT

An improved rotor for use with a segmented peristaltic cartridge comprising a housing and a cover for assembly, said assembled housing and cover defining a pumping chamber which holds the improved rotor, a rotor sleeve and a section of flexible tubing wrapped around the rotor and connected to respective inlet and outlet ports of the cartridge. The flexible rotor includes an eccentric structure wherein flexible beam members provided on an outer surface of the rotor form a compliant member which improves the flexibility of the rotor assembly to avoid excessive compression loads or high torque and/or dynamic leak back or low torque for the tubing in the cartridge.

15 Claims, 4 Drawing Sheets

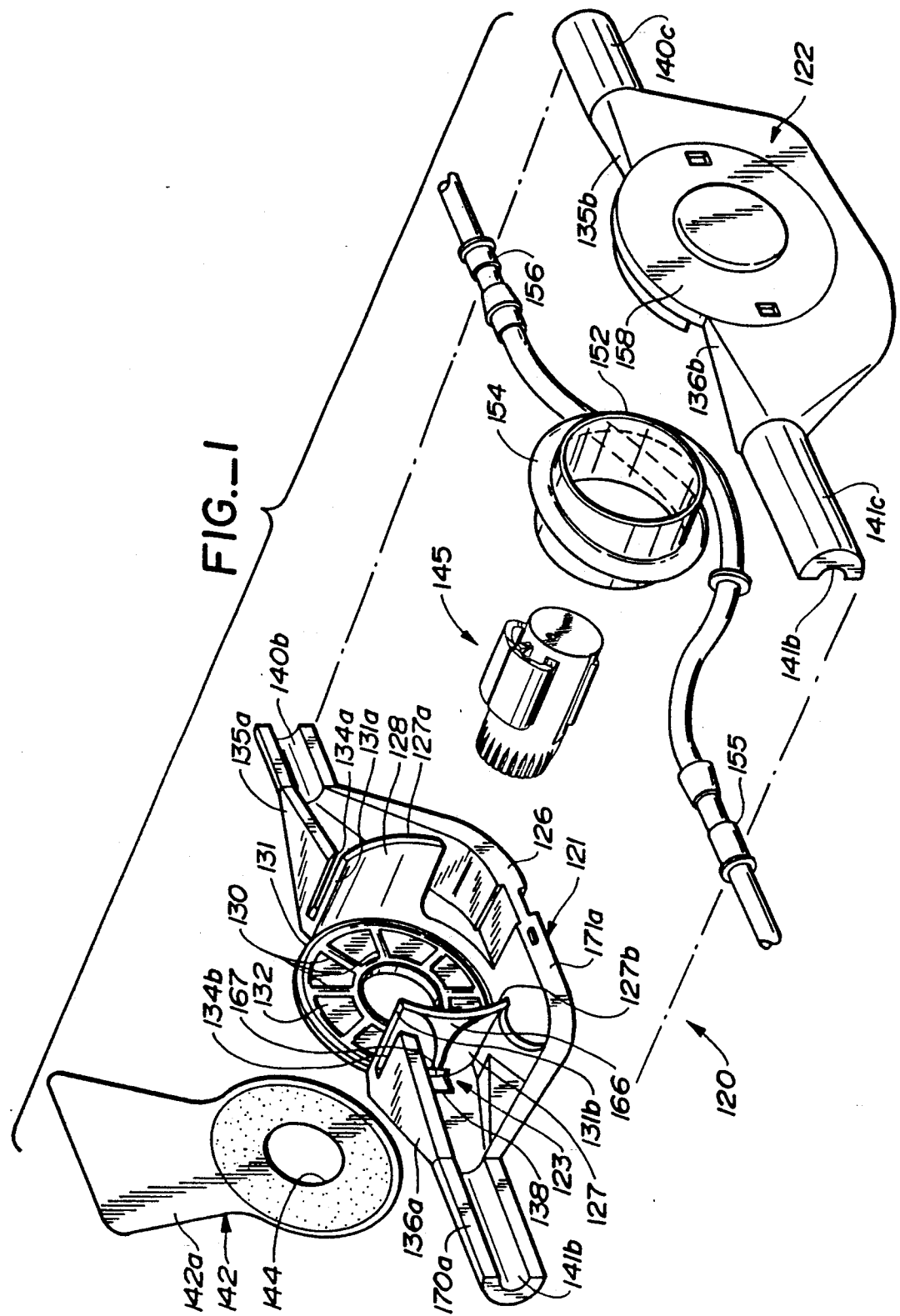

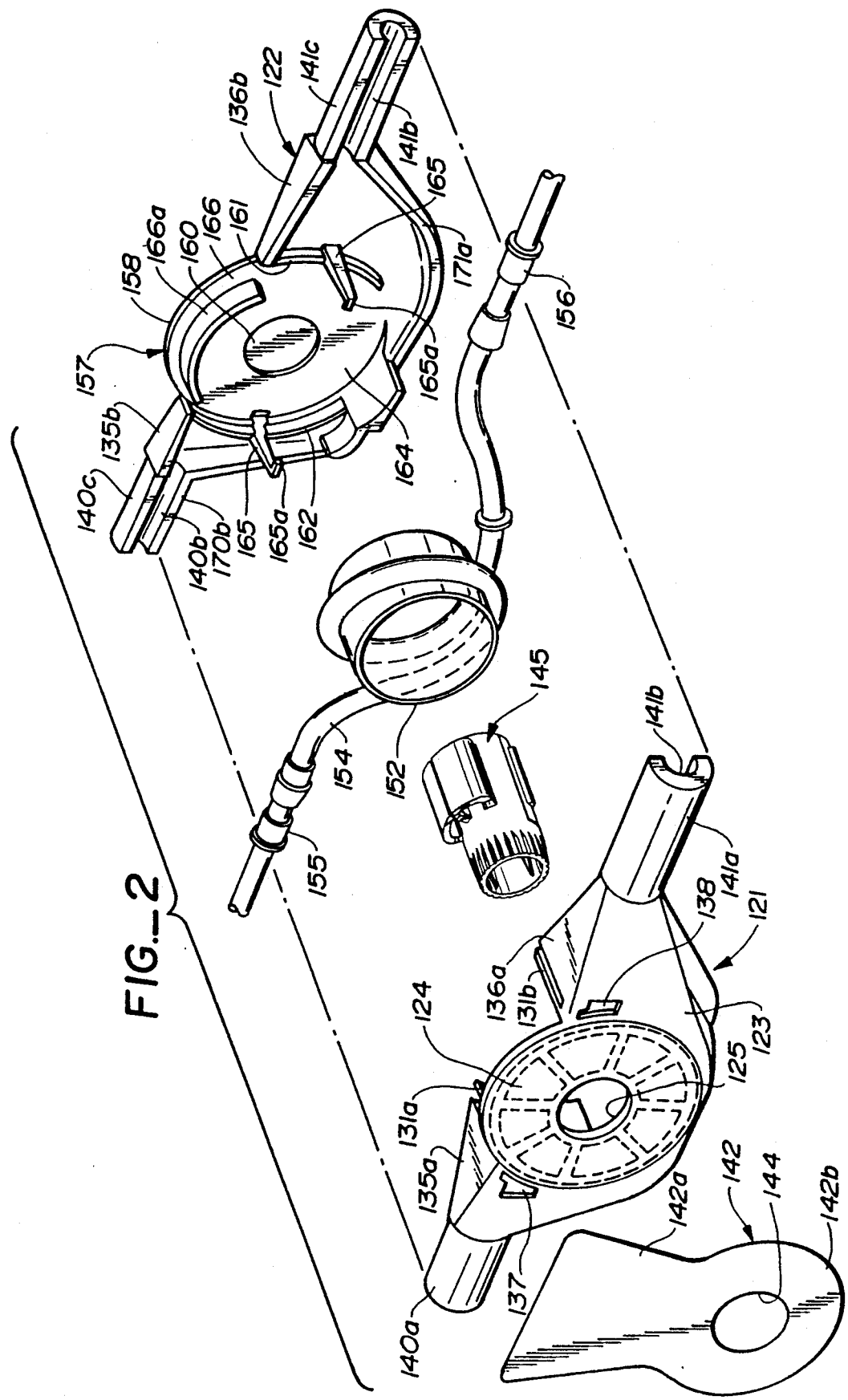
FIG._2

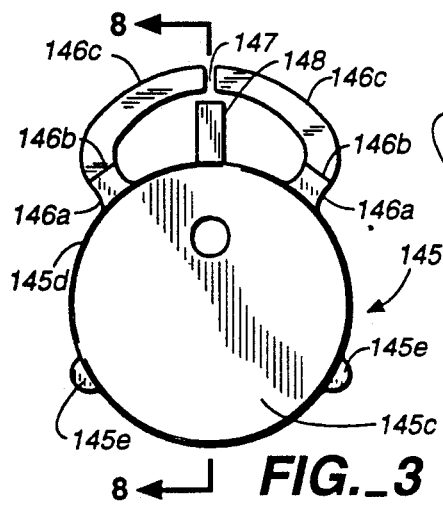
FIG._3
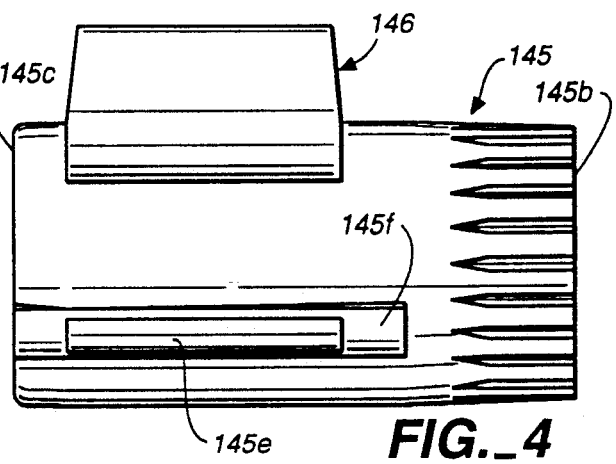
FIG._4
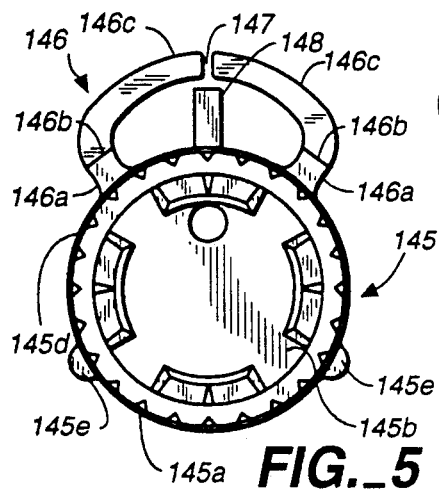
FIG._5
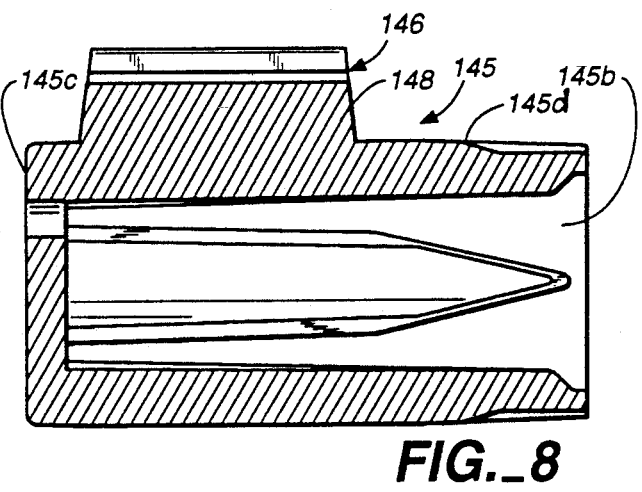
FIG._8
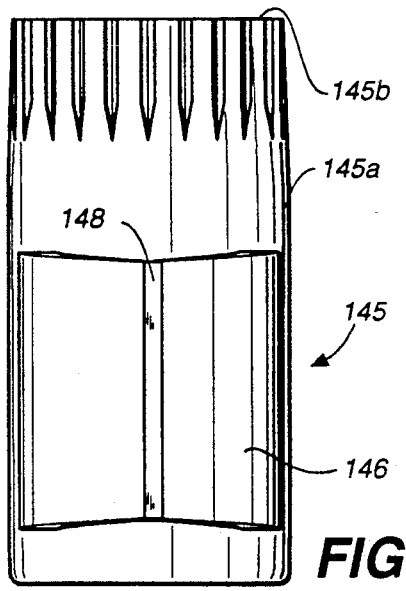
FIG._6
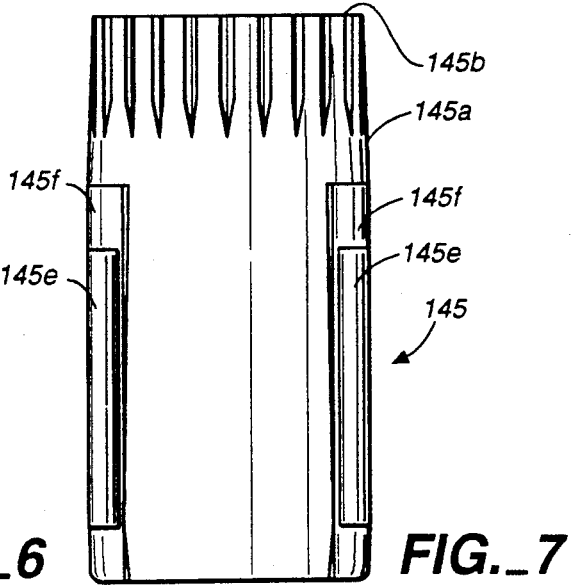
FIG._7

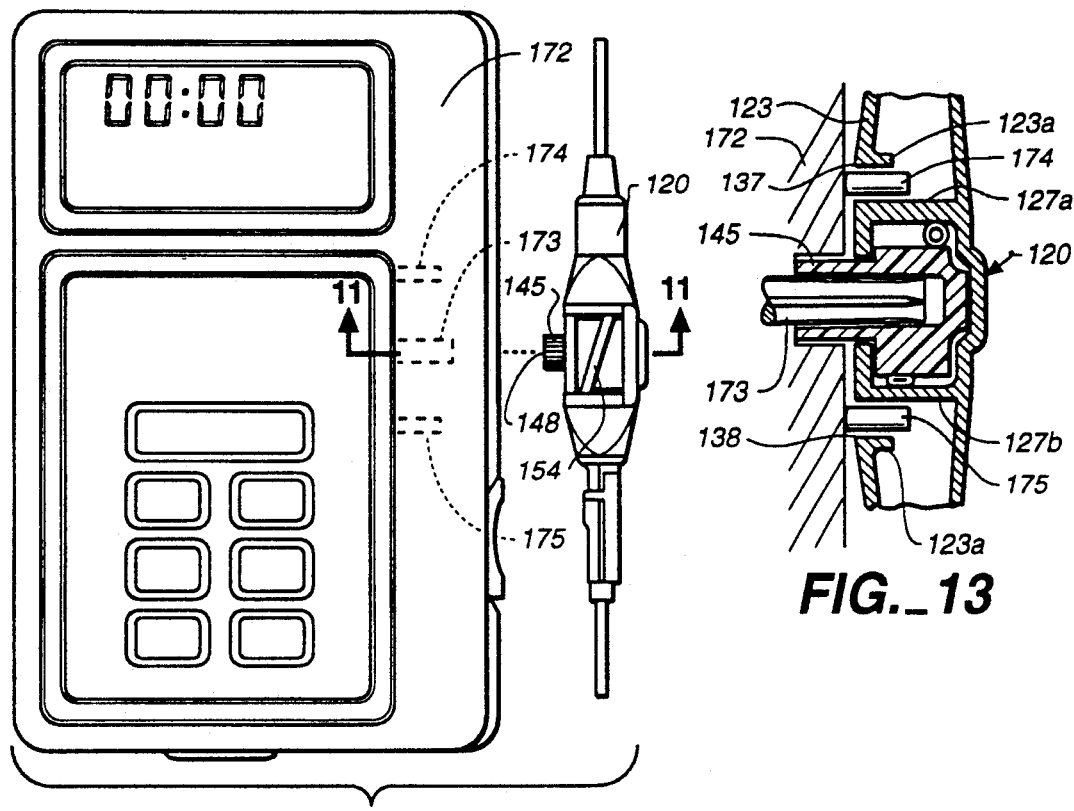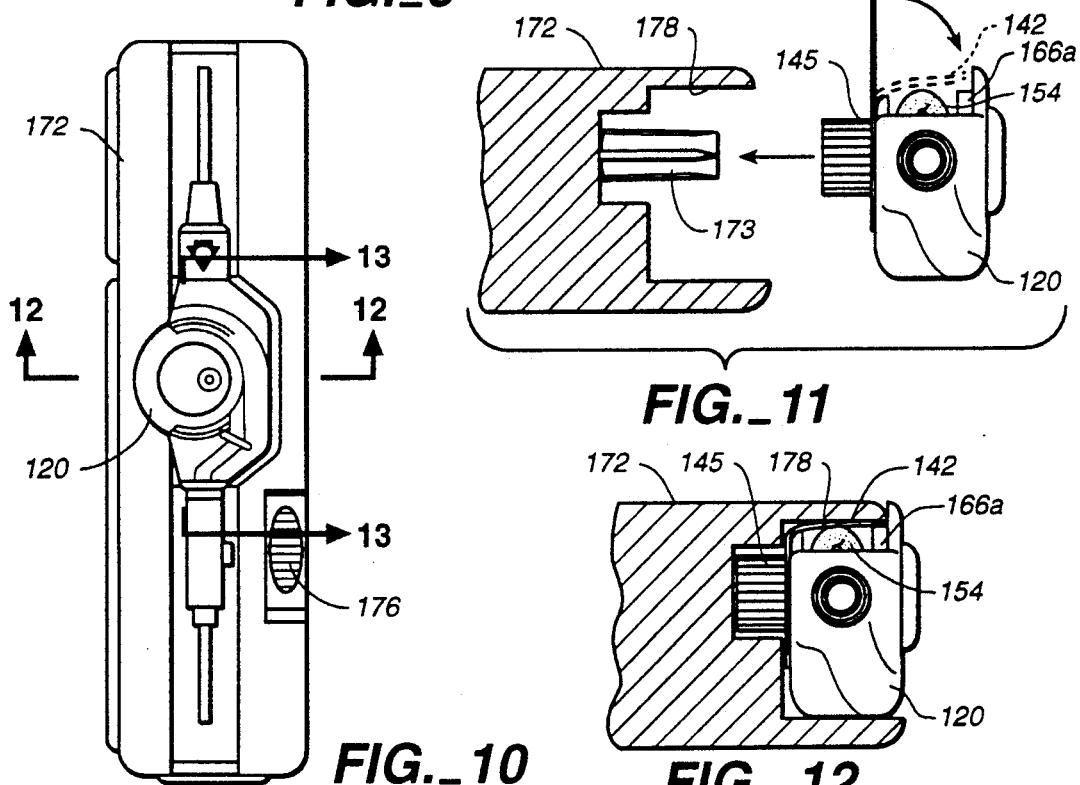

5,326,236

COMPLIANT ROTOR FOR AN IMPROVED CARTRIDGE FOR DRUG INFUSION PUMP

BACKGROUND OF THE INVENTION

A miniature peristaltic pump includes a cartridge received in motor frame, a rotor received in the cartridge, a sleeve mounted on the rotor and a length of compressible tubing having opposite ends, wrapped around the sleeve. The cartridge is formed by two members, the "housing" and the "cover". The rotor is a one-piece rigid member including an eccentric portion which radially squeezes the resilient tubing. The tubing is in a single loop around the rotor sleeve inside the circular pumping cartridge. The cyclic squeezing of the tubing by the rotor and the associated sleeve forces fluid from an inlet port to an outlet port of the pump.

Ideally, a disposable pump cartridge should be assembled and ready for insertion by connecting external inlet and outlet ports to tubing running from the source of medication to the patient. However, the structure of a closed continuous pump cartridge and the eccentricity of the rotor operate to pinch the resilient tubing inside the chamber. Pinching of the tubing can result in a permanent occlusion in the tubing. Further, pinching of the tubing also prevents gravity flushing of air bubbles from the system.

U.S. Pat. No. 4,559,040 focused on an improved cartridge housing wherein a chord segment was removed from the circumference of the pump cartridge housing to prevent the resilient tubing from being pinched at a set position of the rotor high point during storage. With the chord segment of the cartridge housing removed during storage, the tubing remained an open and resilient channel. When the cartridge was prepared for usage, the tubing was readily loaded with medicant by gravity flow because the fluid passage through the tubing in the cartridge is unoccluded. The chord segment was then mounted in place, and the cartridge was inserted into the a motorized drive mechanism (motor frame), wherein a motor shaft of the motor received the rotor of the cartridge to drive the rotor for delivery of medicant to a patient. However, the implementation of the above-described cartridge into a pump motor frame resulted in a modification of the proposed design. The chord segment of the pump chamber removed from the cartridge was integrated into the pump motor frame, eliminating the need for a separate pump chamber segment. However, insertion of a cartridge lacking a portion of its pump chamber into a pump motor frame sometimes resulted in the pinching of tubing between the pump frame and the cartridge at the frame/cartridge interface, producing the occlusions sought to be avoided by the solution described in the above-noted patent.

Additional improvements to the disposable cartridge used in the pump motor frame of a small peristaltic pump used in medical applications, are described in pending U.S. application Ser. No. 996,326, entitled "Improved Cartridge for Drug Infusion Pump," filed Dec. 23, 1992 and assigned to the assignee of the present invention, and to the extend that the prior application is helpful to an understanding of the present invention, such application in its entirety is incorporated by reference herein.

The solutions of the aforementioned patent and patent application focused on improvements in the cartridge housing. However, the improvements in cartridge housing structure did not completely eliminate undesirable variations in fluid flow in the cartridge.

The rotor is a major drive component of the cartridge, disposed within a flexible sleeve which is in constant engagement with the tubing, the rotor/sleeve combination cyclicly squeezing the tubing between the peripheral wall of the cartridge and the rotor to deliver fluid through the pump to the patient.

The rotor plays a key role in the rotary peristaltic infusion cartridge. The rotor/sleeve combination provides the direct interface between the output shaft of the motor drive and compression of the tubing. Within this interface there is no means of compensation for the influence of the outer limits of the design tolerances, which could cause either over-compression (high torque) or under-compression (dynamic leak back) of the tubing. High torque decreases battery life, and dynamic leak back could result in under-infusion.

However, the present rotor is a relatively rigid one-piece plastic member carrying a fixed eccentric member at its outer surface. Moreover, the cartridge housing is a relatively inflexible plastic body having an internal cylindrical cavity of fixed proportions which receives the rotor/sleeve combination. Thus the tubing wrapped around the rotor/sleeve combination is trapped between two substantially rigid members, the cartridge housing and the rotor/sleeve combination, to be cyclically squeezed by said members at substantially high levels of force under relatively inflexible conditions. Relatively slight variations or defects in cartridge housing structure or rotor structure would substantially increase or decrease force levels experienced by the tubing during the pumping cycle, to produce undesirable variations in fluid flow rates, to produce occlusions in the tubing, and to decrease battery life of the pump or to produce undercompression failures, which result in underdelivery of drug to the patient.

The cartridge of the present system would produce improved performance if its inflexible structure could be modified to minimize the effect of variations in structural tolerances, thus to increase compression levels to limit undercompression failures and also to reduce excessive forces exerted on the tubing during the pumping cycle. Because the cartridge housing is a rigid structure having fixed dimensions to maintain a consistent cartridge/motor frame interface, flexibility is not a desirable feature for incorporation into the cartridge housing. Indeed any flexibility built in the cartridge is provided to facilitate the cartridge/motor frame interface, and not to accommodate the rotor chamber within the cartridge housing.

However, it is possible to modify the rotor structure to incorporate a degree of flexibility therein to better enable the cartridge to overcome undesirable manufacturing variations which produce tubing occlusions and undesirable variations in flow rates, whether due to underdesirably low and undesirably high compression forces.

SUMMARY OF THE INVENTION

In a further modification of the improved cartridge as described in aforementioned U.S. application Ser. No. 996,326, an improved rotor is proposed, such a rotor incorporating flexible elements which enable the rotor to accommodate variations in tube stiffness to minimize undesirable variations in fluid flow. Improved rotor flexibility also minimizes the occurrences of occlusions in the tubing, thus also minimizing undesirable interruptions in fluid flow. Pump battery life is also substantially decreased because undesirable high torques produced by excessive compression of the tubing is minimized.

In accordance with the present invention, an improved rotor incorporates a flexible eccentric structure, such structure enabling the rotor to add compliance and compensation to the infusion cartridge device to minimize the occurrence of both high torque and dynamic leak back or low torque situations.

The flexible eccentric structure of the improved rotor of the present invention is mounted on a substantially cylindrical rotor element, closed at one end, and includes, mounted on an outer cylindrical wall of the rotor and near said closed end, a pair of beam elements, each having a base portion mounted on the cylinder wall and a beam member spaced outwardly from the cylinder wall and generally concentric therewith. The respective beam members extend toward each other but do not touch, thus to define a spacing between the end of respective beam members. A stop member projects radially from the outer cylinder wall, generally equally spaced from the respective base portions, with its upper face terminating just below the spacing between the outer ends of the beams, thus to control and limit the inward deflection of the beam portions.

These and other advantages will be better understood when the detailed description set forth below is considered in conjunction with the drawings provided as described below.

BRIEF DESCRIPTION OF THE DRAWINGS

FIG. 1 is an upper right hand exploded perspective view of a peristaltic infusion pump cartridge wherein the improved rotor of the present invention is shown;

FIG. 2 is an upper left hand exploded perspective view of the cartridge shown in FIG. 1, including the improved rotor of the present invention;

FIG. 3 is a front elevation of the improved flexible rotor of the present invention;

FIG. 4 is a side elevation of the improved flexible rotor of FIG. 3;

FIG. 5 is a rear elevation of the improved flexible rotor of FIG. 3;

FIG. 6 is a top elevation of the improved flexible rotor of FIG. 3;

FIG. 7 is a bottom view of the improved flexible rotor of FIG. 3;

FIG. 8 is a sectional view taken along the lines 8—8 of FIG. 3;

FIG. 9 is a top elevational view of a pump motor frame and cartridge in combination, with the cartridge displaced from the pump motor frame;

FIG. 10 is a side elevation of the pump motor frame of FIG. 9, with the cartridge installed;

FIG. 11 is a view partially in section, taken along the lines 11—11 of FIG. 9;

FIG. 12 is a view partially in section, taken along the lines 12—12 of FIG. 10; and FIG. 13 is a view partially in section taken along the lines 13—13 of FIG. 10.

DETAILED DESCRIPTION OF THE PREFERRED EMBODIMENT

To assist in an understanding of the environment in which the improved rotor of the present invention is employed, FIGS. 1 and 2 provide exploded perspective views of the disposable cartridge 120 which receives the improved rotor 145 of the present invention, the cartridge having a housing 121 and a cover 122. The housing 121 comprises a rear wall 123 having a circular central portion 124 having a central opening 125 therein and concentric therewith. Curved side walls 127a and 127b combine with bottom wall 126 to define a central chamber 128 therein.

Central portion 124 of the rear wall 123 includes radially extending ribs 130 which radiate from the central opening 125 to peripheral ribbed edge 131 of the central portion 124 of the rear wall 123. Side walls 127a and 127b include upper edges 131a and 131b which terminate at an outer surface of rear wall 123 to define an open chord segment 132 between upper edges 131a and 131b, the open chord segment 132 being approximately 120° and overlying the chamber 128.

Slot 134a separates side wall 127a from top wall 135a. Slot 134b separates side wall 127b from top wall 136a. Free standing side walls 127a and 128b give the cartridge 120 substantial flexibility and fit. Dowel pin openings 137 and 138 are provided in the rear wall 123 of the housing 121 on opposite sides of central opening 125. Fitments 140a and 141a are provided on opposite ends of rear wall 123 to define respective halves of channels 140b and 141b therein.

Safety shield 142 is a flexible member having an upright flap 142a extending above the top of the cartridge 120. A lower portion 142b of the safety shield 142 generally overlies rear wall 123 with an opening 144 aligned with opening 125 in the rear wall 123.

As viewed in FIGS. 3-8, the improved rotor 145 of the present invention comprises a cylindrical rotor shaft 145a having an open end 145b and a closed end 145c. Cam structure 146 comprises a pair of cantilever beam members 146c supported by respective base portion 146a which extend radially outwardly from an outer wall 145d of the rotor shaft 145a. Each base portion 146a supports at an outer end 146b a respective cantilever beam member 146c, each beam member 146c spaced a common distance from outer wall 145d to be generally concentric therewith. Each beam member 146c projects toward the other, with a spacing 147 of approximately 0.020 inch between respective inner ends of the beam members 146a.

As can best be seen in the top elevation of FIG. 6, each beam member 146c is almost twice as wide as it is long. Projecting radially from the outer wall 145d of the rotor shaft 145a is a stop member 148 which is disposed midway between base portions 146a and extends the width of beam members 146c along the spacing 147. Stop member 148 limits inward flexure of beam sections 146c.

The rotor 145 also includes stabilizer bars 145e, best shown in FIGS. 3-5. Stabilizer bars 145e are longitudinal protrusions mounted on bearing pads 145f (FIGS. 4, 7). Bearing pads 145f have front and rear ends, with the front ends of the bearing pads 145f received in central portion 160 of the cover 122 and the rear ends of the bearing pads 145f received in the opening 125 of the housing 121 (also see FIGS. 1 and 2). The stabilizer bars 145e provide bearing surfaces for the rotor 145 within the cartridge 120.

The eccentric structure 146 is mounted on one side of the outer surface 145d rotor 145 and a stabilizer bar 145e is mounted on each of respective bearing pads 146f opposite eccentric structure 146. The bars 145e improve rotor stability within the cartridge 120, and serve as an aid during cartridge assembly. In FIGS. 3-5, stabilizer bars 145e are about 120° apart and are each about 120° from stop member 148. Other stabilizer placements are possible.

The sleeve 152 (FIGS. 1 and 2) overlies the rotor 145, but is only the length of stabilizer bars 145f and is primarily disposed over eccentric structure 146. A length of flexible tubing 154 is wrapped around the sleeve 152 and, at respective opposite ends of the tubing 154, fittings 155 and 156 define an inlet port 155 and an outlet port 156 for the cartridge 120.

Cover 122 includes a front wall 157 having a circular central portion 158, and a step-down central portion 160 concentric with the circular portion 158. Registration surfaces 161 and 162 complementary to side walls 127a and 127b of the housing 121 are formed on a rear face 164 of front wall 157 of the cover 122. A pair of elongated snap-in members 165 having upper snap-in latches 165a extend upwardly from the rear face 164 of front wall 157 on opposite sides of central circular portion 158 of the cover 122, the snap-in members 165 to be received in a pair of complementary tracking grooves 166 provided on opposite outer surfaces of side walls 127a and 127b, which provides rotational alignment between the housing 121 and the cover 122.

The cover 122 includes top wall portions 135b and 136b which are disposed on opposite side of circular central portion 158 and are complementary with top wall portions 135a and 136a of the housing 121. The top wall portions 135b and 136b engage opposite edges of circular central portion 158 to define an open chord segment 167 of approximately 120° therebetween. A lip 166a conforms generally to the arc of central circular portion 158 and extends rearwardly from the wall 157.

At opposite ends of front wall 157 are provided fitments 140c and 141c which include channel portions 140b and 141b and are complementary to fitments 140a and 141a of the housing 121.

The housing 121 and 122 of the cartridge 120 are assembled by conventional means. Rotor 145 receives the sleeve 152. Tubing 154 is wrapped around the sleeve 152. The assembled rotor 145, sleeve 152 and tubing 154 is then placed in the central chamber 128 of the housing 121, with opposite ends of bearing surfaces 145f of the rotor respectively engaging side cylindrical walls of the step-down portion 160 of the cover 127 and side walls of the opening 125 of the housing 121. The improved rotor 145 of the present invention provides increased flexibility when used in conjunction with the sleeve 152 in the cartridge 120. Such improved flexibility minimizes both overcompression and undercompression failures of the cartridge, i.e., either tubing occlusions or dynamic leak back conditions. Opposite ends of tubing 154 pass under opposite side walls 127a, 127b of the chamber 128 to be received and held in respective channels 140b, 141b of fitments 140a and 141b provided on opposite ends of the rear wall 123. The cover 122 is then snapped into place with snap-in members 165 on the cover 122 engaging complementary snap-fit members 167 provided on the housing 121. The housing and cover are then joined by conventional means, such as ultrasonic welding to form the cartridge 120, in which the rotor 145 is trapped in the chamber 128 in engagement with tubing 154 which has opposite ends 155, 156 trapped in channels 140b, 141b of the housing 121. An alternative configuration of the cartridge 120 eliminates the snap-fit components 165, 166, 167 to join housing 121 and cover 122 by ultrasonic welding only.

FIGS. 9–13 show a pump motor frame 172 receiving an assembled disposable cartridge 120, the cartridge 120 including a safety shield 142. Motor shaft 173 receives the open end 148 of the improved rotor 145 with dowel pins 174 and 175 received in dowel pin openings 137 and 138 respectively of the cartridge 120. The pump motor frame 172 includes a latch 176 (FIG. 10) for latching the cartridge 120 in place.

As seen in the sectional views of FIGS. 11, 12 and 13, shown partially in section, motor shaft 173 engages rotor 145 with safety shield 142 engaged by upper edge 178 of pump motor frame 172 to cause the safety shield 142 to overlie the tubing 154 and the lip 166a to prevent pinching or occluding of the tubing 154 as the cartridge 120 is loaded into the pump motor frame 172. Further, the improved rotor 145 of the present invention includes a flexible eccentric structure 146 to minimize the occurrence of high torque and dynamic leak back situations.

The cartridge 120 may be formed from any suitable material; however, a hard transparent plastic is preferable. It is also preferable to mold the sleeve from a material having a low coefficient of friction. It is also desirable to lubricate the rotor and sleeve to reduce friction. A fluorosilicone lubricant is preferable to reduce friction at the rotor/cartridge interface. The improved rotor of the present invention is a molded one piece part.

I claim:

1. In a segmented peristaltic cartridge comprising a housing, a cover, and an open segment therebetween, said combination defining pump and chamber therein, said cartridge having respective inlet and outlet ports at opposite ends thereof, the housing including a rear segment wherein an arc of approximately 240° forms the internal periphery thereof, the cover, having an arc of approximately 240° which forms the internal periphery thereof, is joined to the housing, a tubing track is created by the space between said housing and said cover, said inlet and outlet ports being formed by the mating of said housing and cover segments, and a pump frame engaging said housing at the open segment thereof and providing a surface completing a missing chord of said tubing track, an improved rotor including an eccentric rotor and rotor shaft disposed in said chamber in the cartridge between said rear housing and said front cover, a sleeve mounted on the rotor, a length of resilient tubing spirally wrapped around said sleeve to be disposed in said tubing track, and having opposite ends engaging respective inlet and outlet ports of the cartridge, the improved rotor including:

a cylindrical body portion including an interior bore received on a motor shaft associated with the motor frame;

an outer cylindrical surface thereof; and an eccentric structure mounted on the outer cylindrical surface of the rotor, said eccentric structure comprising at least one pair of base portions extending generally radially outwardly from the outer cylindrical surface of the rotor and spaced apart on the rotor cylindrical outer surface, a first beam member mounted at one end at the upper end of a first base portion, and an opposite end of the first beam member projecting outwardly from said first base portion, a second beam member having its one end mounted on an upper end of a second base portion, and an opposite end of the second beam member projecting outwardly from said second base portion, both first and second beam members disposed a common distance above the cylindrical outer surface of the rotor and generally concentric therewith, with the respective opposite ends of the beam members projecting toward each other but spaced apart at respective opposite ends thereof whereby in the assembled housing including said housing segment, cover segment, eccentric rotor, rotor sleeve and tube, the eccentric rotor engages said resilient tubing when the cartridge engages the motor frame and the rotor is connected to a rotational drive means, the flexible eccentric structure of the rotor enabling delivery of liquid medicant to a patient with increased reliability.

2. An improved rotor usable in a segmented peristaltic cartridge, the improved rotor disposed in a chamber of the cartridge, a sleeve mounted on the rotor, a length of resilient tubing looped around said sleeve and having opposite ends engaging respective inlet and outlet ports of the cartridge, the rotor comprising:
  a cylindrical body portion including an interior bore;
  an outer cylindrical surface thereof;
  an eccentric structure mounted on the outer cylindrical surface of the rotor, said eccentric structure including at least one pair of base portions extending generally radially outwardly from the outer cylindrical surface of the rotor and spaced apart on the rotor cylindrical outer surface;
  a first beam member mounted at one end at the upper end of a first base portion, an opposite end of the first beam member projecting outwardly from said first base portion; and
  a second beam member having its one end mounted on an upper end of a second base portion, and an opposite end of the second beam member projecting outwardly from said second base portion, both first and second beam members disposed a common distance above the cylindrical outer surface of the rotor and generally concentric therewith, with the respective opposite ends of the beam members projecting toward each other but spaced apart at respective ends thereof;
  the flexible eccentric structure of the rotor enabling delivery of liquid medicant to a patient with increased reliability.

3. The improved rotor as claimed in claim 2 wherein at least one stop member extends generally radially outwardly from the outer surface of the rotor and is interposed between respective first and second base portions to engage and limit inward flexure of respective opposite ends of said first and second beam members.

4. The improved rotor as claimed in claim 3 wherein the stop member is a single member located along a mid-line between said first and second base members.

5. The improved rotor as claimed in claim 2 wherein each of said first and second base portions comprise generally elongated members generally extending along a radial axis of the cylinder at the outer surface thereof.

6. The improved rotor of claim 5 wherein each of respective first and second beam members is substantially wider than each said beam member is long.

7. The improved rotor of claim 6 wherein each of respective first and second beam member is approximately twice as wide as is each said beam member is long.

8. The improved rotor of claim 7 wherein said first beam member is generally equal to said second beam member in length, width and height.

9. The improved rotor of claim 2 wherein at least one rotor stabilizer bar is disposed on the outer cylindrical surface of the rotor, generally opposite the eccentric structure of the rotor to stabilize the rotor during its rotation in the cartridge.

10. The improved rotor of claim 9 wherein two rotor stabilizer bars are placed approximately 120° apart and generally opposite the eccentric structure of the rotor.

11. The improved rotor of claim 2 wherein at least one bearing pad is mounted on the outer cylindrical surface of the rotor, the bearing pad to support a stabilizer bar of the rotor, and opposite ends of the bearing pad are respectively received in the cover and housing of the cartridge.

12. The improved rotor of claim 11 wherein a pair of bearing pads are disposed approximately 120° apart on the outer cylindrical surface of the rotor and generally opposite the eccentric structure of the rotor, each bearing pad receiving and supporting a respective stabilizer bar.

13. The improved rotor of claim 12 wherein each stabilizer bar extends the length of the eccentric structure, and the stabilizer bars engage said sleeve to facilitate assembly of the rotor/sleeve combination.

14. The improved rotor of claim 12 wherein the length of the sleeve approximates the length of the eccentric structure and the stabilizer bars, and the bearing pads extend beyond opposite ends of the eccentric structure and the sleeve thus to better enable the assembly of the housing and cover of the cartridge on the rotor/sleeve combination, and also to stabilize rotation of said combination within the cartridge.

15. An improved rotor usable in a segmented peristaltic cartridge comprising a housing, a cover, and an open segment therebetween, said combination defining a pump and a chamber therein, said cartridge having respective inlet and outlet ports at opposite ends thereof, the housing including a rear segment wherein an arc of approximately 240° forms the internal periphery thereof, the cover, having an arc of approximately 240° which forms the internal periphery thereof, is joined to the housing, a tubing track is created by the space between said housing and said cover, said inlet and outlet ports being formed by the mating of said housing and cover segments, and a pump frame engaging said housing at the open segment thereof and providing a surface completing a missing chord of said tubing track, the improved rotor including an eccentric rotor and rotor shaft disposed in said chamber in the cartridge between said rear housing and said front cover, a sleeve mounted on the rotor, a length of resilient tubing spirally wrapped around said sleeve to be disposed in said tubing track and having opposite ends engaging respective inlet and outlet ports of the cartridge, the improved rotor including:
  a cylindrical body portion including an interior bore received on a motor shaft associated with the motor frame;
  an outer cylindrical surface thereof; and
  an eccentric structure mounted on the outer cylindrical surface of the rotor, said eccentric structure comprising at least one pair of base portions extending radially outwardly from the outer cylindrical surface of the rotor and spaced apart on the rotor cylindrical outer surface, a first beam member carried at the upper end of a first base portion, the first beam member cantilever-mounted on the first base portion, with one end of the first beam member mounted on the first base portion and an opposite end of the first beam member projecting outwardly from said first base portion, a second beam member having its one end mounted on an upper end of a second base portion, and an opposite end projecting outwardly from said second base portion, both first and second beam members disposed a common distance above the cylindrical outer surface of the rotor and generally concentric therewith, with the respective opposite ends of the beam members projecting toward each other but spaced apart at respective opposite ends thereof, whereby in the assembled housing including, with said housing segment, cover segment, eccentric rotor, rotor sleeve and tubing, the eccentric rotor engaging said resilient tubing when the cartridge engages the motor frame and the rotor is connected to a rotational drive means, the flexible eccentric structure of the rotor enabling delivery of liquid medicant to a patient with increased reliability.

* * * * *